United States Patent
Granegger et al.

(10) Patent No.: US 10,828,408 B2
(45) Date of Patent: Nov. 10, 2020

(54) BLOOD PUMP SUPPORTED BY PASSIVE MAGNETIC FORCES

(71) Applicant: Berlin Heart GmbH, Berlin (DE)

(72) Inventors: Marcus Granegger, Perchtoldsdorf (AT); Kim Peter Winterwerber, Berlin (DE); Hendryk Richert, Berlin (DE); Bodo Schmidt, Teltow (DE); Oliver Peters, Berlin (DE)

(73) Assignee: BERLIN HEART GMBH, Berlin (DE)

( * ) Notice: Subject to any disclaimer, the term of this patent is extended or adjusted under 35 U.S.C. 154(b) by 50 days.

(21) Appl. No.: 16/075,557

(22) PCT Filed: Feb. 6, 2017

(86) PCT No.: PCT/EP2017/052549
§ 371 (c)(1),
(2) Date: Aug. 3, 2018

(87) PCT Pub. No.: WO2017/134304
PCT Pub. Date: Aug. 10, 2017

(65) Prior Publication Data
US 2019/0038820 A1    Feb. 7, 2019

(30) Foreign Application Priority Data

Feb. 5, 2016  (DE) ............... 10 2016 001 289
Sep. 29, 2016  (EP) ................... 16191579

(51) Int. Cl.
*A61M 1/10*    (2006.01)
*A61M 1/12*    (2006.01)

(52) U.S. Cl.
CPC ........ *A61M 1/1015* (2014.02); *A61M 1/1086* (2013.01); *A61M 1/122* (2014.02);
(Continued)

(58) Field of Classification Search
CPC ............... A61M 1/27; A61M 1/10; A61M 1/1053–1055
(Continued)

(56) References Cited

U.S. PATENT DOCUMENTS

| 5,507,629 A | 4/1996 | Jarvik |
| 6,015,434 A | 1/2000 | Yamane |

(Continued)

FOREIGN PATENT DOCUMENTS

| CN | 1234854 A | 11/1999 |
| CN | 1886161 A | 12/2006 |

(Continued)

OTHER PUBLICATIONS

English translation of International Search Report issued in International Application No. PCT/EP2017/052549, dated May 8, 2017, pp. 1-3, European Patent Office, Rijswijk, The Netherlands.

(Continued)

*Primary Examiner* — Suzette J Gherbi
(74) *Attorney, Agent, or Firm* — Brinks Gilson & Lione (57) ABSTRACT

A blood pump may be provided that includes an inlet, an outlet and a rotor for delivering fluid from the inlet to the outlet, wherein the rotor is suspended within the blood pump by radial passive magnetic forces and axially is preloaded in one direction at least by way of passive magnetic forces so that, during a fluid-delivering rotation of the rotor, the axial thrust of the rotor acts counter to the magnetic attraction acting axially in the direction of the outlet.

19 Claims, 6 Drawing Sheets

(52) U.S. Cl.
CPC ......... *A61M 1/1017* (2014.02); *A61M 1/1031* (2014.02); *A61M 1/127* (2013.01)

(58) Field of Classification Search
USPC .................................................. 623/3.1–3.29
See application file for complete search history.

(56) References Cited

U.S. PATENT DOCUMENTS

| | | | | |
|---|---|---|---|---|
| 9,827,357 | B2* | 11/2017 | Rodefeld | A61M 1/101 |
| 2009/0234447 | A1* | 9/2009 | LaRose | F04D 13/0666 |
| | | | | 623/3.13 |
| 2010/0268334 | A1* | 10/2010 | Pate | A61M 1/101 |
| | | | | 623/3.14 |
| 2011/0238172 | A1 | 9/2011 | Akdis | |
| 2012/0245680 | A1* | 9/2012 | Masuzawa | F04D 13/0633 |
| | | | | 623/3.11 |
| 2013/0331934 | A1* | 12/2013 | Kabir | A61F 2/24 |
| | | | | 623/3.11 |
| 2014/0336446 | A1* | 11/2014 | Rodefeld | A61M 1/101 |
| | | | | 600/16 |

FOREIGN PATENT DOCUMENTS

| | | |
|---|---|---|
| CN | 104984425 A | 10/2015 |
| WO | WO 97/29795 | 8/1997 |
| WO | WO 98/04834 A1 | 2/1998 |
| WO | WO 2008/017289 A2 | 2/2008 |

OTHER PUBLICATIONS

Chinese Office Action with English translation, dated Aug. 4, 2020, pp. 1-20, issued in Chinese Patent Application No. 201780009907.6, China National Intellectual Property Administration, Beijing, People's Republic of China.

* cited by examiner

b) Section B-B c) Section C-C d)

BLOOD PUMP SUPPORTED BY PASSIVE MAGNETIC FORCES

CROSS-REFERENCE TO RELATED APPLICATIONS

This application is a 371 nationalization of international patent application PCT/EP2017/052549 filed Feb. 6, 2017, which claims priority under 35 U.S.C. § 119 to European patent application 16191579.8, filed Sep. 29, 2016 and German patent application DE 10 2016 001 289.7, filed Feb. 5, 2016. The entire contents of each of the above-identified applications are hereby incorporated by reference.

TECHNICAL FIELD

The present property right relates to a blood pump.

BRIEF DESCRIPTION OF THE DRAWINGS

FIG. 5a shows a side view of a radial pump;
FIG. 5b shows a section B-B from FIG. 5a;
FIG. 5c shows a section C-C from FIG. 5a;
FIG. 5d shows a scaled down perspective view of the pump shown in FIG. 5a;
FIG. 6a shows a side view of a radial pump;
FIG. 6b shows a section B-B from FIG. 6a;
FIG. 6c shows a second C-C from FIG. 6a;
FIG. 6d shows a scaled down perspective view of the pump shown in FIG. 6a;
(FIG. 6a showing a side view, FIG. 6b showing a section B-B from FIG. 6a, FIG. 6c showing a section C-C from FIG. 6a, and FIG. 6d showing a scaled down perspective view of the overall pump.

DETAILED DESCRIPTION

One important property of modern blood pumps is the degree of blood damage. Depending on the pump concept, and in particular the bearing concept, varying degrees of blood damage can occur. On the one hand, as little blood damage as possible is desirable, for example by implementing shapes that favor flow to as great an extent as possible, large gap dimensions and the like. On the other hand, the size of the pump should be limited, in particular in the case of fully implantable pumps. Furthermore, it is desirable to minimize the size of the control unit designed for speed control and for bearing control to as great an extent as possible, while also keeping the related power consumption low.

At present, different bearing types exist for clinically used rotary blood pumps:
1. Mechanical bearings (commercial examples: Heartmate II, Reliant Heart)
2. Hydrodynamic bearings (commercial product: Ventrassist)
3. Hybrid bearings (hydrodynamic and passive magnetic, commercial examples: HVAD, MVAD)
4. Active magnetic bearings (in one or more directions) (commercial examples: INCOR, HM III).

All present bearing configurations have advantages and disadvantages. While the active magnetic bearing, for example, in theory is ideal with respect to blood damage, it is often complex to implement (for example as it relates to the control unit and the power consumption) and associated with additional heat input and/or with substantial secondary flows. On the other hand, hydrodynamic/hybrid bearings are completely passive, which allows a small control unit to be installed and enables low power consumption. The hemocompatibility (or blood damage) of these systems, however, is not necessarily advantageous in terms of their technology due to the very small gap sizes that are present across large areas and is also difficult to implement, especially in the case of axial pumps.

Proceeding from this prior art, it is the object of the present property right to provide a blood pump that not only has a small and energy-saving design, but also causes very low blood damage.

This initially involves a blood pump, comprising an inlet, an outlet and a rotor for delivering fluid, in particular blood, from the inlet to the outlet, wherein the rotor is suspended inside the blood pump by way of radial passive magnetic forces and is, at least passively, repelled or attracted axially in one direction. The blood pump, for example, is configured in such a way that, during a fluid-delivering rotation of the rotor, the axial thrust of the rotor acts counter to the magnetic attraction acting axially in the direction of the outlet.

In this way, a very advantageous passive system is provided with respect to the control unit and the corresponding power consumption as well as the small size of the corresponding components. The rotor is drawn in the direction of the inlet by the axial thrust created by rotors comprising blades or helices or other delivery elements. This force acts counter to the axial passive magnetic force acting purely magnetically. This reduces the load acting on a mechanical bearing, so that the rotor is suspended without forces to as great an extent as possible, and ideally even "levitated." As an alternative, the level of the magnetic preload can be selected in such a way that the mechanical contact between the rotor and the stator is preserved in all conceivable scenarios.

The rotor for example is driven in a contact-free manner by a brushless direct current motor.

According to one refinement, the contact-free portion of the suspension of the rotor takes place exclusively by way of a passive magnetic forces, which is to say that no additional control coils and the like are required for positioning the rotor. As an alternative, however, it is possible to provide an electromagnetic and/or electrodynamic device acting on the rotor, for example so as to enhance the axial thrust of the rotor (which is to say, counter to the delivery direction of the fluid, for example). This can be done, for example, to further reduce the load on the mechanical bearing so as to hold the rotor in a levitating or low-force manner to as great an extent as possible. This may be achieved, for example, by way of appropriate electromagnetic devices or control coils.

According to one refinement, the rotor is additionally supported by a mechanical bearing, in particular for axial support. This mechanical bearing can, in particular, be designed as a contact bearing, and in particular as a tip bearing or ball bearing. This creates a mechanically reliable device, which ensures a stable rotor position, in particular also at low speeds.

As an alternative or in addition, in particular for axial support, the rotor may be additionally supported by a hydrodynamic bearing, which, for example, is also arranged in the outlet-side region of the rotor. Advantageous examples are hydrodynamic bearings in the form of spiral groove bearings.

According to one refinement, an additional bearing, and in particular an axial catcher bearing, is provided for limiting the axial rotor movement. This ensures that the rotor blades or blood contact surfaces of the pump are not damaged as a result of the rotor being drawn excessively in the direction of the inlet during "suctioning" of the pump on a cardiac wall and the attendant high axial thrust.

According to one refinement, the rotor and/or abutting parts of the blood pump are reinforced in the region of at least one additional bearing, in particular with ceramic materials and/or a hard coating, such as diamond-like carbon (DLC).

Blood pumps described above may be used for a variety of bearing concepts, for example for axial pumps/semi-axial pumps (mixed flow pumps) or radial pumps. For example, axial inflow and delivery make take place through the rotor, and axial outflow or tangential outflow may take place in the region of the outlet. All concepts have in common that both the inlet and the outlet can be connected to human or animal blood vessels so as to enhance and/or regulate the natural blood flow.

Further aspects of the present invention will be described hereafter by way of example.

According to one embodiment of a blood pump according to the invention, the blood pump is a pump that can be fully implanted in a human or animal body. This is preferably a pump that is suitable for enhancing and/or regulating the blood circulation of the body. Preferably, the inlet of the pump has an axial design with respect to an axis of rotation of the rotor, the outlet has a radial design with respect to the axis of rotation of the rotor, and/or the rotor of the blood pump has an axial, semi-axial or radial design. In this way, it is possible to easily and reliably support and stabilize different types of rotors.

According to a further embodiment, bearing magnets of the rotor are provided so as to stabilize the rotor radially and axially inside the housing of the blood pump. This means that bearing magnets that co-rotate with the rotor are provided, which assume the stabilizing and/or centering function for the rotor.

According to a further embodiment, the bearing magnets of the rotor are arranged on the side of the rotor facing away from the inlet and/or the bearing magnets are arranged on the side facing the inlet. Depending on whether the rotor has an axial, semi-axial or radial design and/or depending on the flow conditions, maximum flexibility in the design of the blood pump is ensured.

According to a further embodiment, motor coils are provided in the stator of the blood pump and rotor magnets are provided in the rotor, wherein the motor coils are arranged on the side of the rotor facing the inlet and/or on the side of the rotor facing away from the inlet. This ensures maximum flexibility in the configuration of the blood pump.

According to a further embodiment, a mechanical bearing is arranged on the side of the rotor facing the inlet and/or on the side of the rotor facing away from the inlet. In this way, the rotor can be suspended in a variety of ways (preferably counter to the direction of flow of the blood entering through the inlet); however, other arrangements can also be provided, for example a system comprising two bearings, in which closing of the inlet by a rotor moving in the direction of the inlet is prevented.

According to a further refinement, the rotor is connected in the central region thereof to a mechanical bearing by way of struts. This is favorable, for example, for configurations in which only one bearing is provided, and this bearing is provided on the side of the rotor facing the inlet (however, the mounting point can also be connected to the rotor by way of struts on the outlet side).

According to a further embodiment, the blood pump comprises a stator, wherein this embodiment comprises bearing magnets (which are preferably in contact with corresponding bearing magnets of the rotating rotor) in the region of an axis of rotation of the rotor, and wherein the stator moreover comprises a stator element in the region of the axis of rotation of the rotor, a cup of a mechanical bearing being arranged on the tip of the stator element, and additionally rotor magnets of the rotor (preferably in a support plate of the rotor) are arranged and/or motor coils operatively connected to the rotor magnets are arranged in the stator on the side of the rotor facing away from the inlet.

According to a further embodiment, the blood pump is designed as a radial pump comprising struts, wherein a cup of a mechanical bearing which is connected to struts of the rotor is arranged on an elevation of the stator in the region of the axis of rotation of the rotor, and bearing magnets are arranged on the stator side in the stator and bearing magnets arranged in the rotor are provided, preferably on the side of the rotor facing away from the inlet, and furthermore the rotor additionally comprises rotor magnets on the side of the rotor facing the inlet, wherein these rotor magnets cooperate with motor coils in the region of the inlet of the blood pump.

According to a further embodiment, the rotor is attracted by way of passive magnetic forces. As an alternative, it is also possible to provide other configurations (see figures).

According to a further embodiment, the radial distance between at least one rotor-side bearing magnet and at least one stator-side bearing magnet is so small that secure support is also achieved with the smallest possible volume of magnetically active material. The fluid-permeable gap may be ≤50 µm, for example 100 µm (see also FIG. 4, reference numeral 13 in the present property right, for example). The gap between the magnetically active parts can range between 500 µm and 2000 µm, for example, such as 1000 µm, wherein this does not need to be an air gap; non-magnetic materials (appropriate plastic materials, for example) can be present in this gap; for details or definitions, reference is made to the introductory part of the description of the present property right).

According to a further embodiment, the blood pump does not comprise an inlet guide vane connected upstream of the rotor. In embodiments in which only one bearing is provided, which supports the rotor counter to the flow direction, it is possible to select such an embodiment (having a simple design), in particular when the magnetic arrangement of the bearing magnets or a suitable interaction between the motor coils and the magnets of the rotor providing the motive power is ensured inside the blood pump.

According to a further embodiment, the bearing magnets of the rotor are fastened in cantilevers of the rotor which are fastened to the rotor base body by way of struts, wherein these rotor-side bearing magnets interact with bearing magnets of the stator located radially outside the bearing magnets of the rotor so as to radially and/or axially stabilize the rotor inside the blood pump.

According to a further refinement, the motor for providing the motive power of the rotor is designed as a pancake motor.

A further aspect relates to the placement of permanent magnets in the blades of the rotor. This results in a reduction of the magnetic air gap. As a result, blades made of magnetic material and/or blades comprising permanent magnets therein shall be considered to be disclosed for all embodiments shown in the present patent application (regardless of the type of bearing that is provided).

Figure 1:
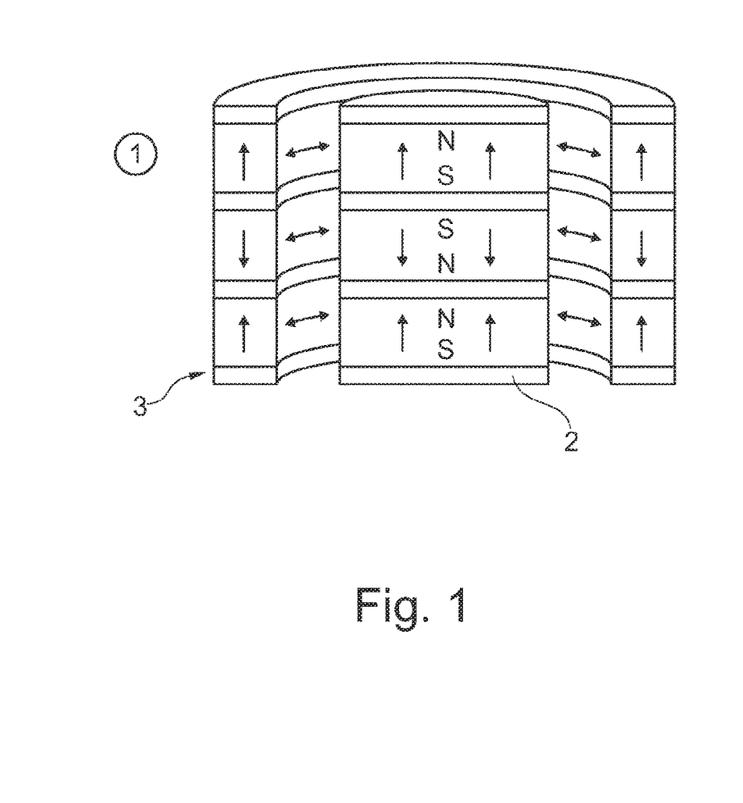
FIG. 1 shows a cross-section of a bearing having a magnet configuration that enables a radial passive magnetic force and preloading in the axial direction.
Figure 2:
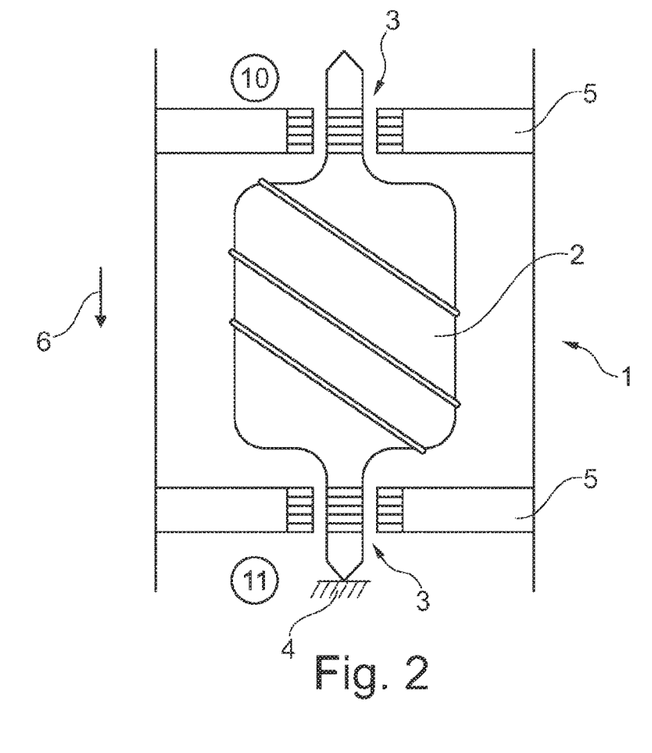
FIG. 2 shows an example of a blood pump that comprises an additional mechanical bearing in the outlet-side region of the rotor.
Figure 3:
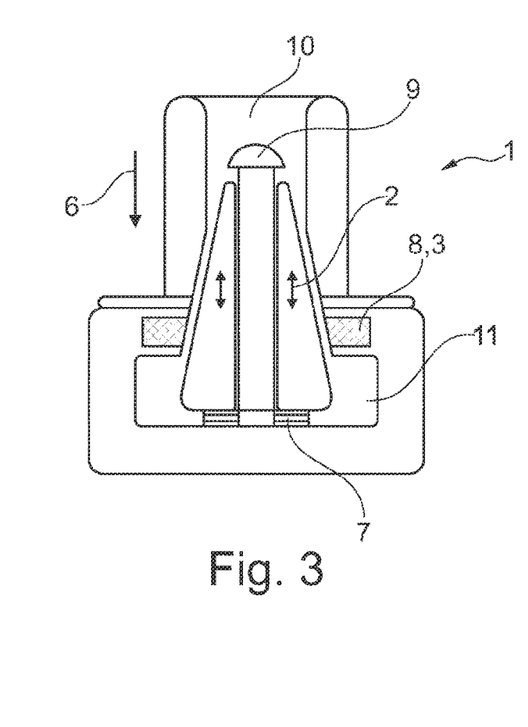
FIG. 3 shows a further example of a blood pump that comprises a hydrodynamic bearing in the outlet-side region of the rotor.
Figure 4:
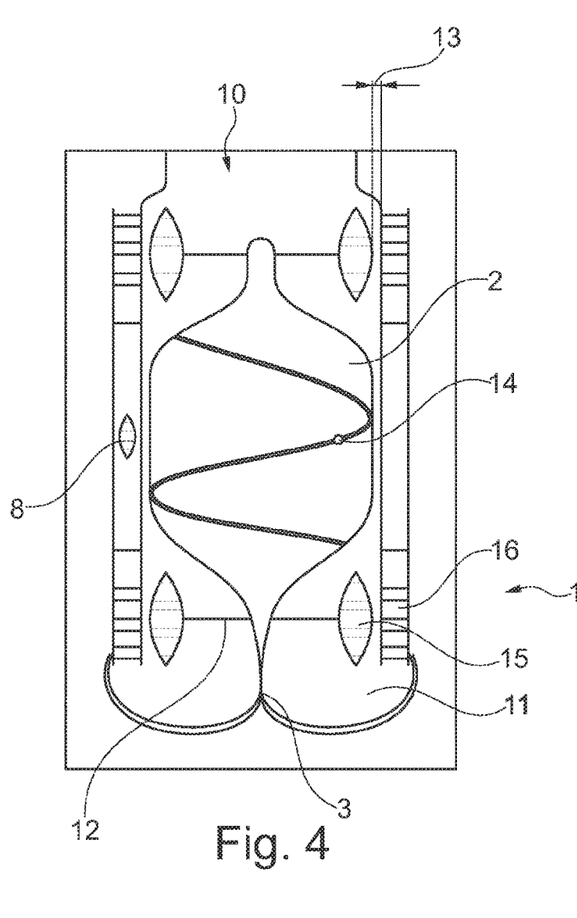
FIG. 4 shows a further example of a blood pump that comprises a mechanical bearing in the outlet-side region of the rotor.

The invention will be described hereafter based on several drawings. In the drawings:

FIG. 1 shows a cross-section of a bearing having a magnet configuration that enables a radial passive magnetic force and preloading in the axial direction;

FIG. 2 shows an example of a blood pump that comprises an additional mechanical bearing in the outlet-side region of the rotor;

FIG. 3 shows a further example of a blood pump that comprises a hydrodynamic bearing in the outlet-side region of the rotor;

FIG. 4 shows a further example of a blood pump that comprises a mechanical bearing in the outlet-side region of the rotor. This pump has the magnets positioned in such a way that the pump does not require an inlet guide vane. So as to achieve the highest possible stiffness, the rotor-side ring magnets are attached to the interacting magnets as close to the pump tube as possible. The ring magnets are connected to the rotor or attached to the blades by way of struts.

Figure 5:
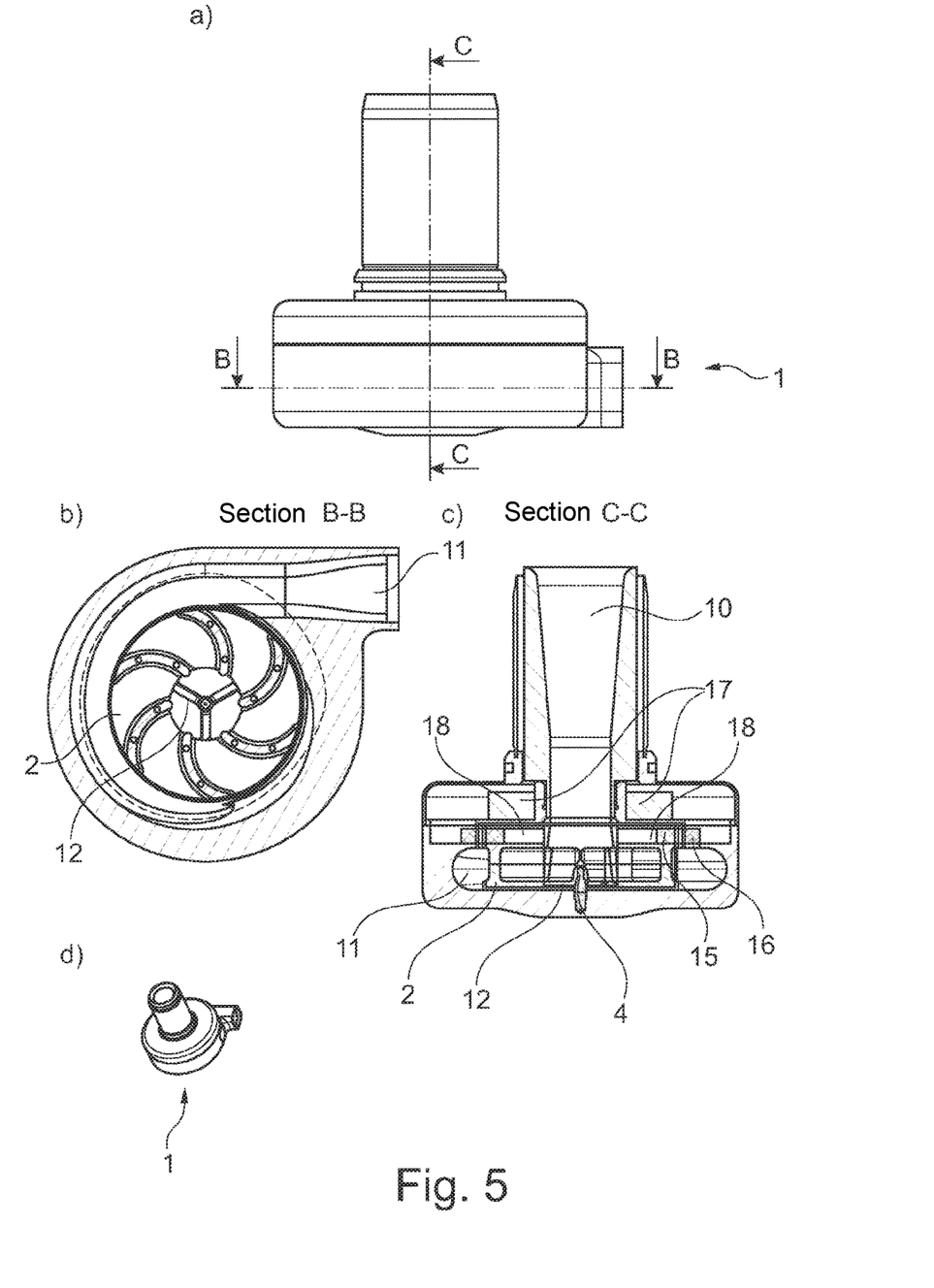
Figure 6:
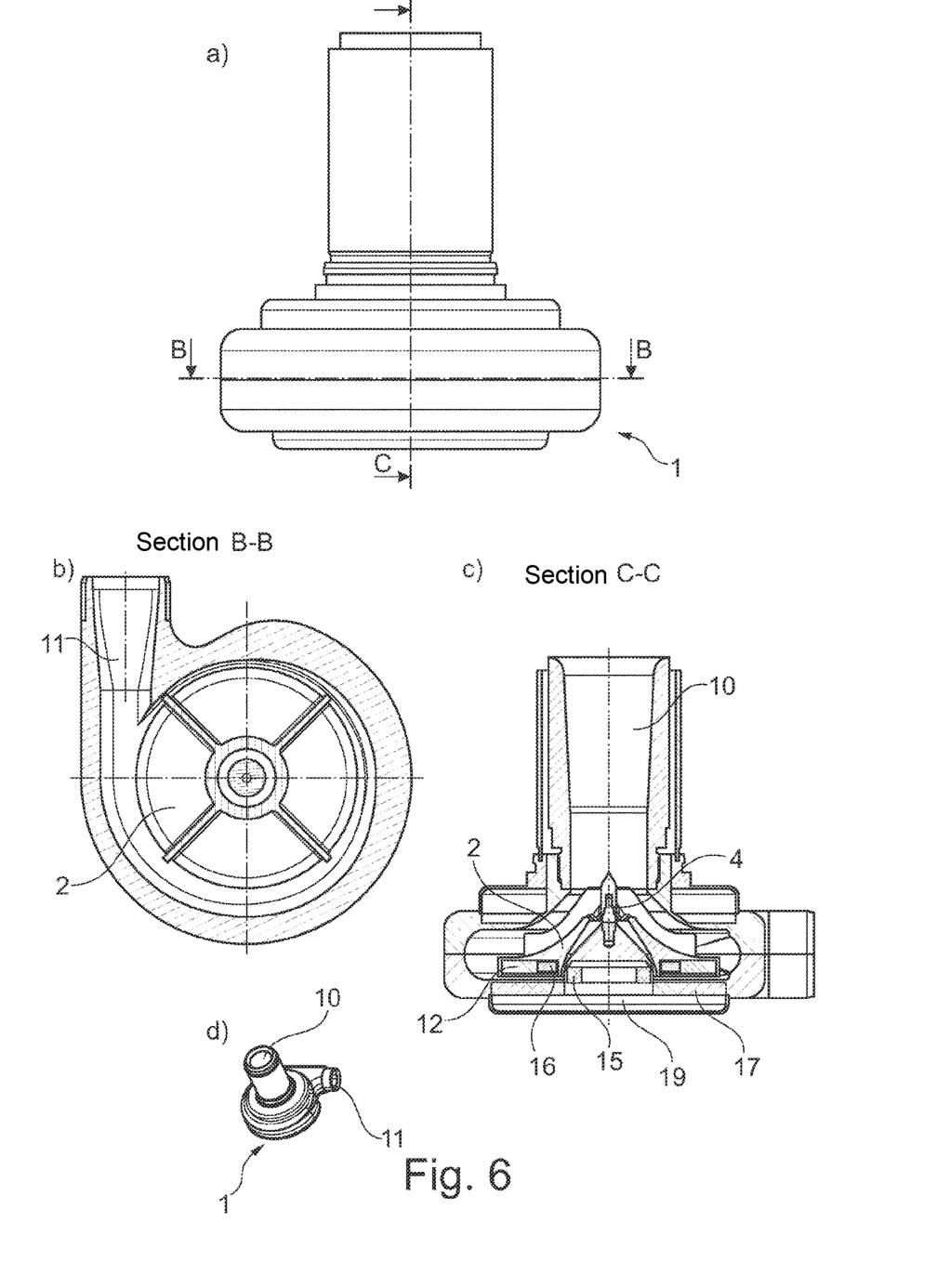
Figure 7:
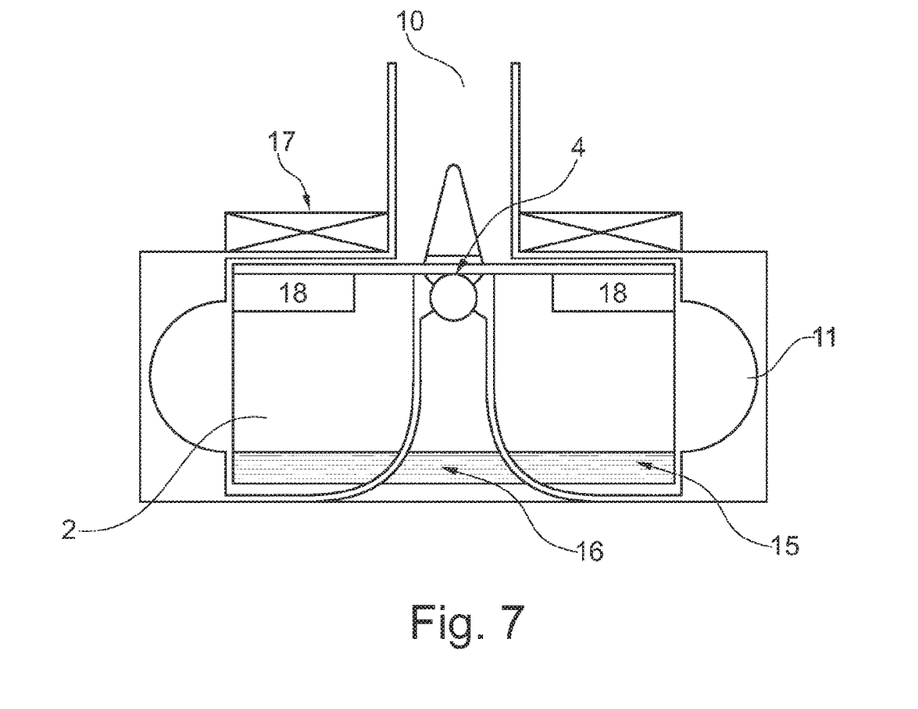
FIG. 7 shows a cross section of an example of a blood pump in which an axial inlet and a radial outlet are provided.

FIGS. 5 to 7 show examples of radial blood pumps that comprise a mechanical bearing and are magnetically preloaded opposite to the inlet. In these embodiments as well, the ring magnet configuration can be similar to that in FIG. 1. Again, force is removed from the mechanical bearing in exemplary embodiments as a result of the axial thrust. The mechanical bearing is connected to a spindle in the center of the pump by way of thin struts, for example, which rotate together with the rotor. In examples, the motor is designed as a pancake motor, and the motor magnets are accommodated in the lower cover plate. The pump can also be designed with an upper cover plate so as to be able to exert additional, repelling magnetic forces that interact with the housing on the rotor. Such a pump should always ensure mechanical contact of the contact bearing.

Figure 8:
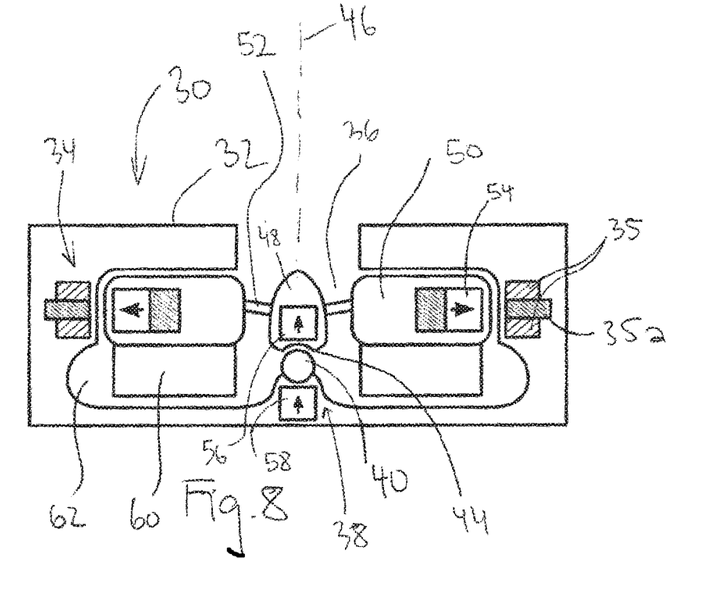
FIG. 8 shows a further schematic illustration of a pump according to the present application.

FIG. 8 shows a further schematic illustration of a pump according to the present application.

FIG. 1 shows a blood pump 1 in the region of a bearing 3. The arrows shown in FIG. 1 indicate the orientation of the layered magnets; however, this shall only be understood by way of example, without defining a resulting magnetic force direction. In particular, it is apparent from FIG. 1 how a portion of a rotor 2 is held radially in a ring of the bearing 3 by a radial passive magnetic force, and preloading in a desired axial direction is achievable. Examples for the use of such a bearing are shown in the following figures.

FIG. 2 shows such a blood pump 1, in which a rotor 2 is mounted. For this purpose, bearings 3 (according to FIG. 1, for example) held on respective struts (inlet guide vane or diffuser) 5 are provided in the region of the inlet 10 and of the outlet 11. A flow (which is to say a fluid flow) in the direction of the arrow 6 is created by the rotation of the rotor. The rotor is driven by a motor, which is not shown here.

The blood pump 1 thus includes an inlet 10 and an outlet 11, wherein the rotor 2 is designed for delivering fluid (in direction 6) from the inlet to the outlet. The rotor 2 is suspended by radial passive magnetic forces inside the blood pump 1 and axially is attracted (preloaded) in the direction of the outlet 11 at least by way of passive magnetic forces, so that the axial thrust of the rotor acts counter to the acting magnetic preload during a fluid-delivering rotation of the rotor 2. This means that the flow takes place from the inlet 10 to the outlet 11 in direction 6, and the axial thrust of the rotor acts in the opposite direction.

FIG. 2 additionally shows a mechanical bearing in the outlet-side region of the rotor, which is present in the form of a contact bearing 4 (designed as a tip bearing here). This enables exact positioning or centering of the rotor, for example at low speeds, with comparatively little friction. In the region of the tip bearing, a portion of the rotor or abutting surfaces of the blood pump are made of hard materials (such as gemstones, for example ruby, sapphire, diamond, DLC or ceramics) so as to further minimize the friction here and increase the durability.

FIG. 3 shows an alternative design of a blood pump. Again, an axial inlet 10 is shown. Furthermore, an outlet chamber or an outlet 11 is shown, which enables blood to flow out tangentially/laterally. The rotor 2 is suspended by radial magnetic forces in a bearing 3 (see FIG. 1) and is axially preloaded in one direction. The rotor is driven in a contact-free manner by a motor 8. Additionally, a catcher bearing 9 is shown, which prevents the rotor 2 from jamming or sliding out of the blood pump housing when the inlet 10 is suctioned on a cardiac wall.

FIG. 3 furthermore shows a hydrodynamic bearing 7 on the outlet-side end of the blood pump. This is a spiral groove bearing, for example, which makes contact with abutting regions of the housing of the blood pump, for example at low speeds (at which the hydrodynamic properties do not fully take effect yet). Ceramic and/or DLC materials are also provided in this region to reduce friction and/or to increase the service life. At the operating speed of the blood pump, the hydrodynamic bearing takes effect (which is to say direct contact no longer exists). The additional axial thrust of the rotor supports the hydrodynamic bearing and reduces the load thereon. The following features may also apply to the rotor of FIG. 3:

A blood pump (1), comprising an inlet (10), an outlet (11) and a rotor (2) for delivering fluid from the inlet (10) to the outlet (11), wherein the rotor (2) is suspended within the blood pump (1) by radial passive magnetic forces and axially is attracted or repelled in one direction at least by way of passive magnetic forces, preferably in such a way that, during a fluid-delivering rotation of the rotor (2), the axial thrust of the rotor acts counter to the magnetic attraction acting axially in the direction of the outlet.

The present property right furthermore relates to the following aspects, some of which have already been briefly addressed above.

One aspect is to develop, for example, an axial (or semi-axial or radial) rotary blood pump (small control unit) that is preferably passively supported, comprising no large surface-area hydrodynamic bearing.

This object is achieved, for example, in that an axial/semi-axial or radial pump is supported by radial passive magnetic forces (if necessary using a supporting hydrodynamic component), and that a passive magnetic preload in one direction is also present axially. The axial thrust, which is present anyhow and dependent on the pressure differential, acts in the opposite axial direction. With an ideal design of the pump and appropriate adaptation of the outlet housing/diffuser, positive axial thrust will always be present in human circulatory system, and the rotor can thus levitate without the use of an additional bearing. The axial support is helped by a one-sided mechanical or hydrodynamic bearing.

An inlet-side mechanical catcher bearing for when the axial thrust becomes too great (during suctioning on the cardiac tissue) can be ensured by way of material combinations (ceramics, hard coating, such as DLC).

The magnetic axial preload can also be selected to be so strong that contact is made with the axial mechanical bearing even in the worst-case scenarios (suctioning).

The radial passive magnetic force and the preloading in an axial direction can be achieved by way of the magnet configuration shown in FIG. 1, for example.

The axial preloading can also be implemented by additional attracting or repelling magnets.

The following refinements of the present invention are possible, among other things:
1. Radial support: Magnetically supported journal bearings having a large gap (for example, ≤100 μm).
   Axial support: passive magnetic (preloading in the direction of the outlet) and mechanical bearing on the outlet side. The mechanical bearing can take on axial, radial or other forms of sliding bearings (see FIG. 2, for example). The axial thrust generates forces in the direction of the inlet. If necessary: mechanical (catcher) bearing in the direction of the inlet.
2. Radial support: Magnetically supported sliding bearings having a large gap (>100 μm).
   Axial support: passive magnetic, axial thrust and, where necessary, hydrodynamic bearing. The hydrodynamic bearing (see FIG. 3) can be implemented in the form of a spiral groove bearing or by ramps and the like on the rotor or on the housing.
3. Blood pump that comprises a mechanical bearing in the outlet-side region of the rotor. This pump has the magnets positioned in such a way that the pump does not require an inlet guide vane. So as to achieve the highest possible stiffness, the rotor-side ring magnets are attached as close as possible to the pump tube with the interacting magnets. The ring magnets are connected to the rotor or attached to the blades by struts.
4. Blood pumps that comprise a mechanical bearing and are magnetically preloaded in the direction of the outlet. In this design as well, the ring magnet configuration is the same as that described above (FIG. 1). Again, force is removed from the mechanical bearing as a result of the axial thrust. The mechanical bearing is connected to a spindle in the center of the pump by way of thin struts, which rotate together with the rotor. In the embodiments, the motor is designed as a pancake motor, and the motor magnets are accommodated in the lower cover plate. The pump can also be designed with an upper cover plate so as to be able to exert additional, repelling magnetic forces that interact with the housing on the rotor. Such a pump must always ensure mechanical contact of the contact bearing.

Hereafter, FIGS. 4 to 7 additionally will be described in detail.

FIG. 4 shows an example of an axial blood pump 1 comprising a rotor 2. The rotor comprises blading in the form of blades 14. The rotor comprises rotor magnets, which are not shown in greater detail and cooperate with a motor or motor coils 8 of a stator of the blood pump 1. The rotor magnets can be accommodated in the blades 14; as an alternative, these may also be provided further to the radial inside in the rotor, wherein the efficiency of the motor may then be slightly lower.

The stator has a substantially tubular design, comprising an inlet 10 and a non-axial outlet 11. A bearing 3, which is designed as a sliding bearing, such as an axial or radial bearing, is provided on the side of the rotor facing away from the inlet. The bearing is arranged in such a way that the flow entering through the inlet 10 subjects the bearing to pressure. The blades 14 are oriented in such a way that pressure relief with respect to the bearing 3 takes place during a delivering movement of the rotor 2. Bearing magnets of the rotor 15 and bearing magnets of the stator 16 are provided so as to additionally stabilize the rotor radially and axially inside the stator of the blood pump. The bearing magnets of the rotor 15 are fastened to cantilevers of the rotor by way of struts 12. The corresponding cantilevers in which the bearing magnets 15 are accommodated can have a circular ring-shaped design, for example; it is also possible for individual satellites to be provided, which are distributed across the circumference of the circle. Such cantilevers may be provided on corresponding struts both on the inlet side and on the outlet side. The advantage of this arrangement is that (regardless of the blading) good radial and axial stabilization of the rotor inside the stator can be achieved. For this purpose, it is favorable when a gap 13 is as small as possible, for example 50 μm, but less than 200 μm, preferably less than 150 μm, and particularly preferably less than 100 μm.

In the arrangement shown in FIG. 4, it is achieved by way of the struts 12 (which are rod-shaped, for example, and allow liquid to pass through) that not only good stabilization of the rotor 2 is provided in the region of the cantilevers or the bearing magnets 15/16, but also relatively unimpaired through-flow of fluid (preferably blood) is possible despite the small gap widths 13.

FIG. 5 (FIG. 5a showing a side view, FIG. 5b showing a section B-B from FIG. 5a, FIG. 5c showing a section C-C from FIG. 5a, and FIG. 5d showing a scaled down perspective view of the overall pump comprising an inlet 10 and an outlet 11; the inlet 10 being designed for the attachment to a cannula or a blood vessel, which also applies to the outlet 11) shows a fully implantable blood pump comprising an intracorporeal radial pump including magnets and a motor inside a pump housing. An axial inlet and a radial outlet are provided in the housing. The rotor 2 is supported on a mechanical bearing 4, which is designed as a contact bearing and has a particularly low-friction design, wherein the material pairing comprises ceramic materials and/or a hard coating, for example DLC. The portion of the rotor that is being supported is connected to the remaining rotor by way of struts 12. The rotor is designed to be hollow in some regions, which is to say it comprises oblique/radial delivery blades, which deliver fluid entering axially through the inlet 10 radially to the outside. The rotor 2 has a substantially disk-shaped design, wherein the bearing is arranged in the lower region and, in the region thereabove, the channels or blades providing the fluid delivery are provided, and above that (which is to say in the direction of the inlet) the rotor magnets 18 are provided, which cooperate with motor coils 17 provided axially thereabove (which is to say further in the direction of the inlet 10) for driving the rotor 2 located in the stator. This has the advantage that preferably few moving elements are provided and only electromagnetic actuation of the rotor inside the housing of the blood pump takes place. This not only requires low maintenance, but also has a simple configuration.

In addition, rotor-side bearing magnets 15 and stator-side bearing magnets 16 are provided, which are provided to radially and axially stabilize the rotor inside the housing of the blood pump. Again, the bearing is arranged in such a way that the rotor is pressed against the bearing 4 under fluid pressure and when the rotor is stopped, and the pressure on the bearing 4 is relieved when fluid is being delivered through the rotor 2. It shall be pointed out again that the layered design of the rotor enables a clear and simple design, wherein rotor magnets 18 and rotor-side bearing magnets 15 are accommodated in a cover plate of the rotor and cooperate with corresponding stator-side elements (motor coils 17 or stator-side bearing magnets 16).

FIG. 6 (FIG. 6a showing a side view, FIG. 6b showing a section B-B from FIG. 6a, FIG. 6c showing a section C-C from FIG. 6a, and FIG. 6d showing a scaled down perspective view of the overall pump comprising an inlet 10 and an outlet 11; the inlet 10 being designed for the attachment to a cannula or a blood vessel, which also applies to the outlet 11) shows a further embodiment in which again an axial inlet 10 and a radial outlet 11 are shown. This is a semi-axial pump comprising a central stator element, in which stator-side bearing magnets 16 are installed and on the tip of which the cup of a mechanical bearing 4 is seated. The motor coils 17 are located in the housing, which is to say on the stator side in the blood pump 1; these cooperate with rotor magnets 18 accommodated in the lower portion of the rotor 2. If necessary, this rotor 2 can also comprise an additional cover plate. As a result, this is a blood pump 1 comprising a stator 19, wherein bearing magnets of the stator are arranged in the region of an axis of rotation of the rotor 2, and wherein the stator 19 comprises a stator element in the region of the axis of rotation of the rotor 2, a cup of a mechanical bearing being arranged on the tip of the stator element, and additionally rotor magnets 18 of the rotor are preferably arranged in a support plate of the rotor 2 and/or motor coils 17 operatively connected to the rotor magnets are arranged in the stator 19 on the side of the rotor 2 facing away from the inlet 10.

FIG. 7 shows a further embodiment of a blood pump 1 in which an axial inlet 10 and a radial outlet 11 are provided. On the side facing the inlet, the rotor 2 comprises rotor magnets 18, which cooperate with motor coils 17 in the housing of the blood pump 1 for the motive power for the rotor. Rotor-side bearing magnets 15 are attached on the side of the rotor facing away from the inlet, which cooperate with stator-side bearing magnets 16 so as to radially and axially stabilize the rotor inside the blood pump. Additionally, a mechanical bearing 4 is provided, in which struts 12 that allow liquid to pass through in the direction from the inlet 10 to the outlet 11 are provided and enable additional mechanical mounting or support of the rotor. This is a blood pump 1 designed as a radial pump comprising struts 12, wherein a cup of a mechanical bearing which cup is connected to struts 12 of the rotor 2 is arranged on an elevation of the stator 19 in the region of the axis of rotation of the rotor 2, and bearing magnets 16 are arranged on the stator side in the stator 19 and rotor-side bearing magnets 15 are preferably arranged on the side of the rotor 2 facing away from the inlet 10, and furthermore rotor magnets 18 are preferably arranged on the side of the rotor 2 facing the inlet, which rotor magnets 18 cooperate with motor coils 17 in the region of the inlet 10 of the blood pump.

FIG. 8 shows another variant of a pump. For the sake of clarity, the inlet is not shown. The outside of the pump resembles the appearance of the pump illustrated in FIG. 5a or 6a.

The pump 30 comprises a base body 32, which accommodates a motor stator 34 comprising a stator winding 35 and a stator core 35a, and moreover includes a rotor chamber 36. The motor stator 34 revolves around the rotor chamber 36. The rotor chamber 36 moreover comprises an outlet (not shown), which essentially corresponds to one of the outlets from FIGS. 5 and/or 6. An elevation 38, having a ball or a conical section of a ball 40 arranged on the tip thereof, is located centrally in the rotor chamber 36. With respect to the ball, the arrangement thereof and the materials thereof, reference is made to the EP application EP 16191613.5, for example, which is hereby incorporated in its entirety in the present application by reference.

A rotor 42, which includes a cup 44 corresponding to the ball 40 on the bottom side thereof, is arranged in the rotor chamber 36 so that the rotor 42 is able to rotate on the ball 40 about the axis 46. The rotor 42 itself is shaped so as to be able to rotate freely about the axis 46 in the rotor chamber. The only connection between the rotor chamber 36 and the rotor 42 is provided by the ball 40. A support or pivot bearing is formed between the rotor 42 and the ball 40.

The rotor 42 comprises a central body 48 and an annular body 50. The two bodies are non-rotatably connected to one another by way of a plurality of struts 52. Permanent magnets 54 are arranged in the annular body, which are aligned so as to be able to set the rotor 42 in motion by way of the motor stator 34. Axially aligned permanent magnets 56 and 58 are arranged in the central body 48 and in the elevation 38, respectively, which bring about an axially attracting force and axially preload the pivot bearing. This prevents the rotor 42 from being drawn upward in the figure during the pumping process. Optionally, the permanent magnets 56 and 58 furthermore form a passive radial bearing, which counteracts the rotor 42 giving way radially.

On the bottom side of the annular body 50, the rotor 42 comprises blading 60, which can be designed similarly to the blading illustrated in FIG. 5, for example. The rotor chamber 36 can comprise a bulge 62 at the height of the blading so as to improve the transport of blood to the outlet. The shown pump can have a very small height since the base body, due to the motor stator 34 revolving radially around the rotor chamber, essentially only has to have the height of the rotor chamber, in addition to the corresponding wall thickness of the wall surrounding the rotor chamber. While this increases the radial dimension of the base body, the axial height can be considerably reduced and/or the size of the rotor chamber can be increased, so that the rotor, at low revolutions, is able to deliver a volume of blood that is comparable to a small rotor chamber, which in turn reduces the blood damage.

Tilting the rotor about the ball is stabilized by the interaction of the forces from the attracting magnetic bearing 56, 58 and the aligning passive magnetic forces from the motor. An aligning torque acts between the motor magnets and the motor stator due to the reluctance forces, or an aligning moment acts due to the magnetic forces of the magnetic bearing.

The present invention relates to the following aspects, among other things:
1. A blood pump (1), comprising
   an inlet (10),
   an outlet (11) and
   a rotor (2) for delivering fluid from the inlet (10) to the outlet (11), wherein the rotor (2) is suspended within the blood pump (1) by radial passive magnetic forces and axially is attracted in the direction of the outlet (11) at least by way of passive magnetic forces, preferably in such a way that, during a fluid-delivering rotation of the rotor (2), the axial thrust of the rotor acts counter to the magnetic attraction acting axially in the direction of the outlet.
2. The blood pump according to aspect 1, characterized in that the rotor (2) is attracted purely by way of passive axial magnetic forces.
3. The blood pump according to any one of the preceding aspects, characterized in that an electromagnetic and/or electrodynamic device acting on the rotor (2) is provided so as to enhance the axial thrust.
4. The blood pump according to any one of the preceding aspects, characterized in that the rotor (2) is additionally supported by a mechanical bearing (4), in particular for axial support.
5. The blood pump according to aspect 4, characterized in that the mechanical bearing (4) is arranged in the inlet-side and/or outlet-side region of the rotor (2).
6. The blood pump according to either aspect 4 or 5, characterized in that the mechanical bearing (4) is designed as a contact bearing, and in particular as a tip or ball bearing.
7. The blood pump according to any one of the preceding aspects, characterized in that the rotor (2) is additionally supported by a hydrodynamic bearing (7), in particular for axial support.
8. The blood pump according to aspect 7, characterized in that the hydrodynamic bearing (7) is arranged in the outlet-side region of the rotor (2).
9. The blood pump according to either aspect 7 or 8, characterized in that the hydrodynamic bearing (7) is designed as a spiral groove bearing.
10. The blood pump according to any one of the preceding aspects, characterized in that an additional bearing, and in particular a catcher bearing, is provided for limiting the axial rotor movement in the direction of the inlet (10).
11. The blood pump according to any one of aspects 4 to 10, characterized in that the rotor (2) and/or abutting parts of the blood pump are reinforced in the region of at least one additional bearing, in particular with ceramic materials and/or DLC.

The bearing technology shown in the present property right can represent a platform of small, passive rotary blood pumps having high hemocompatibility and comprising a small control unit and the like.

LIST OF REFERENCE NUMERALS (Excerpt, Applicable to All Embodiments in the Drawings Unless Denoted Otherwise)
1 blood pump
2 rotor
3 bearing
4 contact bearing
5 struts (extending from the pump tube)
6 direction of an arrow
7 hydrodynamic bearing/spiral groove bearing
8 motor
9 catcher bearing
10 inlet
11 outlet
12 struts (on the rotor)
13 gap
14 blades of the rotor
15 bearing magnets, rotor
16 bearing magnets, stator
17 motor coil
18 rotor magnets
19 stator
30 pump
32 base body
34 motor stator
35, 35a stator winding or core
36 rotor chamber
38 elevation
40 ball
42 rotor
44 cup
46 axis
48 central body
50 annular body
52 struts
54, 56, 58 permanent magnets
60 blading
62 bulge

The invention claimed is:

1. A blood pump, comprising
an inlet,
an outlet,
an additional bearing comprising a catcher bearing arranged to limit axial rotor movement in a direction of the inlet, and
a rotor for delivering fluid from the inlet to the outlet, wherein the rotor is suspended within the blood pump by radial passive magnetic forces to axially attract or repel in one direction at least by way of passive magnetic forces, so that during a fluid-delivering rotation of the rotor, axial thrust of the rotor acts counter to magnetic attraction acting axially in a direction of the outlet.

2. The blood pump according to claim 1, wherein the rotor is attracted by way of passive axial magnetic forces.

3. The blood pump according to claim 1, wherein an electromagnetic device, an electrodynamic device, or both act on the rotor to enhance the axial thrust.

4. The blood pump according to claim 1, wherein the rotor is additionally supported by a mechanical bearing for axial support,
wherein the mechanical bearing is arranged in a region on an inlet-side of the rotor, a region on an outlet-side of the rotor or both.

5. The blood pump according to claim 1, wherein the rotor is additionally supported axially by a hydrodynamic bearing, wherein the hydrodynamic bearing is arranged in an outlet-side region of the rotor.

6. The blood pump according to claim 1, wherein the rotor, abutting parts of the blood pump, or both, are reinforced in a region of the additional bearing with ceramic materials, a hard coating comprising diamond-like carbon (DLC).

7. The blood pump according to claim 1, wherein the blood pump is a pump that is fully implantable in a human or animal body, and
wherein the inlet of the blood pump has an axial design with respect to an axis of rotation of the rotor and the outlet has a radial design with respect to the axis of rotation of the rotor.

8. The blood pump according to claim 1, further comprising a plurality of bearing magnets of the rotor, which are positioned to stabilize the rotor radially and axially inside a housing of the blood pump.

9. The blood pump according to claim 8, wherein the bearing magnets are arranged on a side of the rotor facing away from the inlet or the bearing magnets are arranged on a side of the rotor facing the inlet.

10. A blood pump comprising:
an inlet;
an outlet;
a rotor for delivering fluid from the inlet to the outlet, wherein the rotor is suspended within the blood pump by radial passive magnetic forces to axially attract or repel in one direction at least by way of passive magnetic forces, so that during a fluid-delivering rotation of the rotor, axial thrust of the rotor acts counter to magnetic attraction acting axially in a direction of the outlet;
a stator;
a plurality of motor coils included in the stator of the blood pump, and
rotor magnets included in the rotor, wherein the motor coils are arranged on a side of the rotor facing the inlet or on a side of the rotor facing away from the inlet.

11. The blood pump according to claim 1, further comprising a mechanical bearing arranged on a side of the rotor facing the inlet, and/or on a side of the rotor facing away from the inlet.

12. The blood pump according to claim 1, wherein the rotor is connected by struts, in a central region of the blood pump, to a mechanical bearing.

13. The blood pump according to claim 1, wherein the blood pump includes a stator, wherein bearing magnets of the stator are arranged in a region of an axis of rotation of the rotor, and wherein the stator comprises a stator element in a region of the axis of rotation of the rotor, a cup of a mechanical bearing is arranged on a tip of the stator element, and additionally a plurality of rotor magnets of the rotor are arranged in a support plate of the rotor.

14. A blood pump comprising:
an inlet;
an outlet; and
a rotor for delivering fluid from the inlet to the outlet, wherein the rotor is suspended within the blood pump by radial passive magnetic forces to axially attract or repel in one direction at least by way of passive magnetic forces, so that during a fluid-delivering rotation of the rotor, axial thrust of the rotor acts counter to magnetic attraction acting axially in a direction of the outlet, wherein the blood pump is designed as a radial pump comprising struts of the rotor and a stator, wherein a cup of a mechanical bearing which is connected to the struts of the rotor is arranged on an elevation of the stator in a region of the axis of rotation of the rotor, and bearing magnets are arranged on a stator side in the stator and rotor-side bearing magnets are arranged on a side of the rotor facing away from the inlet, and furthermore a plurality of rotor magnets are arranged on the side of the rotor facing the inlet, which cooperate with motor coils in the region of the inlet of the blood pump.

15. The blood pump according to claim 4, wherein the mechanical bearing comprises a sliding bearing operable as an axial bearing, a radial bearing, or both.

16. The blood pump according to claim 5, wherein the hydrodynamic bearing comprises a spiral groove bearing.

17. The blood pump according to claim 7, wherein the rotor of the blood pump comprises an axial, semi-axial or radial design.

18. The blood pump according to claim 13, further comprising motor coils operatively connected to the rotor magnets and arranged in the stator on a side of the rotor facing away from the inlet.

19. The blood pump according to claim 14, further comprising a plurality of bearing magnets arranged on a stator side in the stator, and a plurality of rotor-side bearing magnets arranged on a side of the rotor facing away from the inlet, wherein the bearing magnets, the rotor-side bearing magnets, and the rotor magnets cooperatively operate with the motor coils in a region of the inlet of the blood pump.

* * * * *